United States Patent [19]

McDonald

[11] Patent Number: 5,843,188

[45] Date of Patent: Dec. 1, 1998

[54] ACCOMMODATIVE LENS IMPLANTATION

[75] Inventor: Henry H. McDonald, 8 Whittier Ct., Rancho Mirage, Calif. 92270

[73] Assignees: Henry H. McDonald; William W. Haefliger, both of Pasadena, Calif.; a part interest

[21] Appl. No.: 954,656

[22] Filed: Oct. 20, 1997

[51] Int. Cl.⁶ .................................................. A61F 2/16
[52] U.S. Cl. ................................................................ 623/6
[58] Field of Search .................................................. 623/6

[56] References Cited

U.S. PATENT DOCUMENTS

| | | | |
|---|---|---|---|
| 4,198,714 | 4/1980 | Jensen | 623/6 |
| 4,304,012 | 12/1981 | Richard | 623/6 |
| 4,414,694 | 11/1983 | Choyce | 623/6 |
| 4,441,217 | 4/1984 | Cozean, Jr. | 623/6 |
| 4,573,998 | 3/1986 | Mazzocco | 623/6 |
| 4,585,456 | 4/1986 | Blackmore | 623/6 |
| 4,605,409 | 8/1986 | Kelman | 623/6 |
| 4,731,078 | 3/1988 | Stoy et al. | 623/6 |
| 4,769,035 | 9/1988 | Kelman | 623/6 |
| 4,786,445 | 11/1988 | Portnoy et al. | 623/6 X |
| 4,790,846 | 12/1988 | Christ et al. | 623/6 |
| 4,813,957 | 3/1989 | McDonald | 623/6 |
| 4,816,031 | 3/1989 | Pfoff | 623/6 |
| 4,834,751 | 5/1989 | Knight et al. | 623/6 |
| 4,840,627 | 6/1989 | Blumenthal | 623/6 |
| 4,842,602 | 6/1989 | Nguyen | 623/6 |
| 4,880,426 | 11/1989 | Ting et al. | 623/6 |
| 4,888,013 | 12/1989 | Ting et al. | 623/6 |
| 4,888,014 | 12/1989 | Nguyen | 623/6 |
| 4,894,062 | 1/1990 | Knight et al. | 623/6 |
| 4,932,970 | 6/1990 | Portney | 623/6 |
| 4,938,767 | 7/1990 | Ting et al. | 623/6 |
| 4,957,505 | 9/1990 | McDonald | 623/6 |
| 4,959,070 | 9/1990 | McDonald | 623/6 |
| 4,978,354 | 12/1990 | Van Gent | 623/6 |
| 5,030,231 | 7/1991 | Portney | 623/6 |
| 5,044,743 | 9/1991 | Ting | 623/6 X |
| 5,098,444 | 3/1992 | Feaster | 623/6 |
| 5,108,429 | 4/1992 | Wiley | 623/6 |
| 5,171,266 | 12/1992 | Wiley et al. | 623/6 |
| 5,203,788 | 4/1993 | Wiley | 623/6 |
| 5,203,789 | 4/1993 | McDonald | 623/6 |
| 5,203,790 | 4/1993 | McDonald | 623/6 |
| 5,217,464 | 6/1993 | McDonald | 606/107 |
| 5,258,025 | 11/1993 | Fedorov | 623/6 |
| 5,395,378 | 3/1995 | McDonald | 606/107 |
| 5,405,385 | 4/1995 | Heimke et al. | 623/6 |
| 5,476,514 | 12/1995 | Cumming | 623/6 |
| 5,480,428 | 1/1996 | Fedorov et al. | 623/6 |
| 5,578,081 | 11/1996 | McDonald | 623/6 |

FOREIGN PATENT DOCUMENTS 4131229  1/1993  Germany .

OTHER PUBLICATIONS

"Polyseudophakia" by Harry B. Grabow published Jul., 1977, pp. 1–6.

"Achieving Emmtropia in Extremely Short Eyes With Two Piggyback Posterior Chamber Intraocular Lenses", by Jack T. Holladay et al, published in Ophthalmology, vol. 103, No. 7 Jul. 1996, pp. 1118–1123.

"Two Iols Better Than One For High Hyperopes" by Leslie Sabbagh, published Nov. 1, 1994, Ophthalmology Times.

"Implanting Two Posterior Chamber Intraocular Lenses in Microthalmos" by Dr. J. L. Gayton, published in Ocular Surgery News, 1994, pp. 64 & 65.

*Primary Examiner*—Mary Beth Jones
*Attorney, Agent, or Firm*—William W. Haefliger

[57] ABSTRACT

A method of providing an artificial lens inserted into the eye between the iris and the natural lens zone, there being eye ciliary muscles located peripherally of the zone, that includes providing the artificial lens to be compliant and to have anterior and posterior surfaces, and haptics extending away from the periphery of the artificial lens; and inserting the artificial lens to extend into position between the iris and the zone, and to cause the haptics to extend into adjacency to the ciliary muscles, and; allowing the haptics to adhere to the ciliary muscles; whereby subsequent movement of the ciliary muscles causes movement of the haptics transmitted to effect bodily movement of the lens in posterior and anterior directions to change the angularity of refraction of light passing through the lens toward the eye retina.

31 Claims, 3 Drawing Sheets

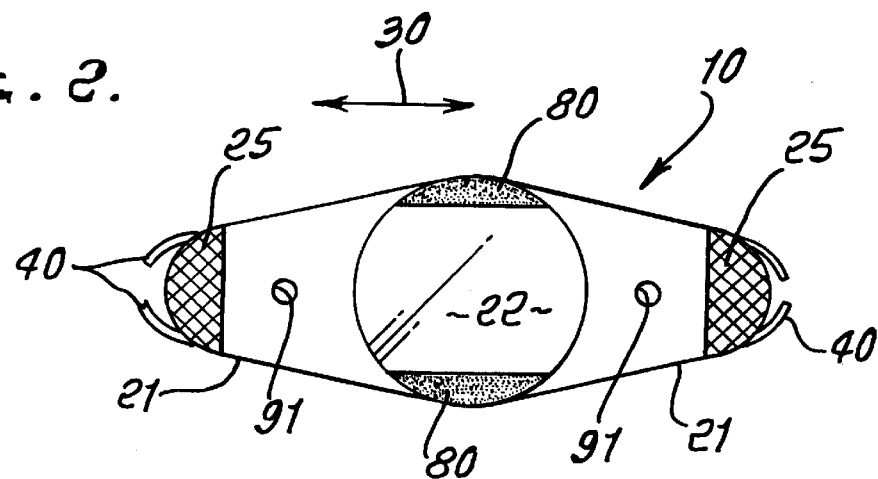
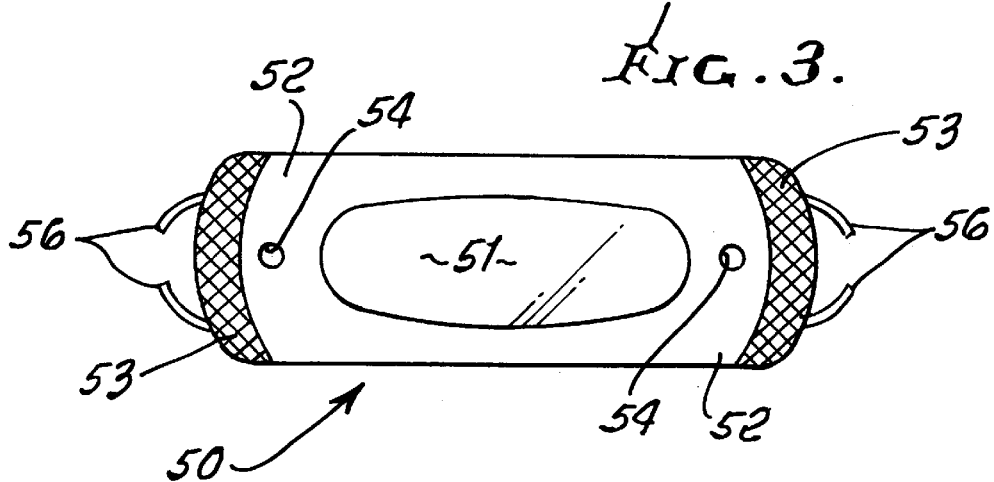
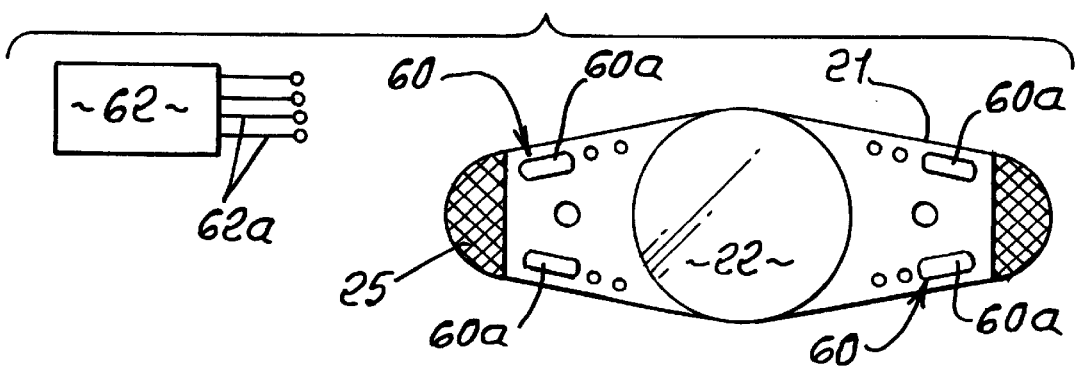

ACCOMMODATIVE LENS IMPLANTATION

BACKGROUND OF THE INVENTION

This invention relates generally to implantation of artificial lenses in the eyes of humans, and/or animals, and more particularly concerns implantation of such lenses in the posterior chambers of the eyes, i.e., between the iris and the natural lens zone. That zone may contain a natural lens, or an artificial lens, such as a pseudophakic lens.

It is known to insert artificial lenses into posterior chambers of eyes; however, prior implantations have suffered from difficulties. These have included presumed need for attaching or anchoring the artificial lens directly onto a surface of the pseudophakic lens, as by bonding, or by clipping mechanism. These expedients can or do interfere with vision and lens movement. There is need for method and apparatus that avoids such problems and difficulties. There is also need for implantation of lenses capable of movement toward or away from the natural lens zone as will be referred to herein.

SUMMARY OF THE INVENTION

It is a major object of the invention to provide implantation of a vision correcting artificial lens into the eye posterior chamber, and in such manner as to avoid problems and difficulties, as referred to. Basically, the method of the invention includes the steps:

a) providing the artificial lens to be compliant and to have anterior and posterior surfaces, and haptics extending away from the periphery of the artificial lens, b) and inserting the artificial lens to extend into position between the iris and the natural lens zone, and to cause the haptics to extend into adjacency to the ciliary muscles, and c) allowing the haptics to adhere or attach to the ciliary muscles, to move in response to ciliary muscle movement.

Such adherence may be achieved by adherence of haptic outer surfaces to zonular ligaments and/or onto fascia of the ciliary muscles, thereby positioning the artificial lens close to the surface of the pseudophakic lens; and so that clarity of vision is not interrupted by bonding zones, or clip devices to hold the lens in place, such bonding and clips not being needed.

It is another object to position the inserted lens in the manner referred to whereby subsequent movement of the ciliary muscles causes movement of the haptics, transmitted to effect bodily movement of the lens in posterior and anterior directions, to change the angularity of refraction of light passing through the lens toward the eye retina, i.e., adapting to near and far vision.

The invention achieves one or more of the following advantages:

a) enables haptics to be placed in the uncluttered territory of the anterior aspect of the posterior ciliary sulcus;

b) allows placement of an elongated, asymmetric lens implant across the eye chamber to position the haptics for fixation onto zonular ligaments and/or into the fascia of the ciliary muscle;

c) affords conforming of a lens implant posterior surface over the pseudophakic lens, with haptics that extend laterally to anchor onto the available plateau at the ciliary sulcus, the fascia of the ciliary muscle, and/or onto the inert zonular ligaments;

d) allows haptics to achieve a distinctive leverage over and control of the lens optic segment, even with a mildly weak ciliary muscle;

e) affords the opportunity of using the advantages of the clear, temporal corneal wound for lens insertion without previous scarring;

f) provides an axis of astigmatism, and prisms, or other means, for correcting diplopia with particular haptic edge designs;

g) provides separability of the implanted lens from the pseudophakic lens, to:
  1) enable recoverability of the lens with ease, if necessary;
  2) maintain eye aqueous humor lateral flow behind the implanted lens without need for a central apical puncture or hole, which can detract from the clear vision;
  3) separated independent functioning of the implanted lens, without impairment from the encased pseudophakic lens entrapped in the lens capsule;
  4) allows laser titrateable (effected) alterations in the supportive elastimed band of an elongated, rectangular (i.e., asymmetric) lens implant, such as adjustments to accommodate to:
     a) the need for sufficient separability of the lens implant;
     b) the need for lens re-positioning, post-operatively;
     c) the stiffness of the haptics in control of the optic segment, as desired;

h) provides for more natural passage of aqueous humor between the pseudophakic and implanted lenses; accommodation of the lens implant is enhanced by conformance to the natural lens configuration that exists, particularly in the realm of the autonomic nerve system, and pertaining to accommodative reflex;

i) components for the errancy of the pseudophakic lens needs, such as light-blocking function of the lens implant for glare and U-V exposure, in addition to refractive corrections for astigmatism, diplopia, anisometropia, and for severe and mild degrees of myopia and hyperopia, and loss of accommodation;

j) use of the implant lens can become preferred, in view of the case of a five minute, very accurate, operative implant procedure, which is readily reversible, if ever necessary, and having the added advantage of quick relief of pain and restoration of clear vision in hours, and full rehabilitation by the next morning;

k) the range of useful indications for this lens implant are startling and may require or enable a combination of seven to eight different lens implants in one lens implant procedure, to achieve a desired vision result;

l) the ciliary muscle having a leveraged effect on the optic segment through the angle of approach of the lateral and posterior design and stiffening of the haptic, as well as adhesive, restraint on the optic segment to prevent excessive forward advancement of the optic segment by the addition of adhesive haptic edges, which also thickens the A-P diameter of the lens to assist in accommodation.

A further object includes detecting and modifying a physical characteristic of the lens inserted into the eye. Miniature electronic circuitry implants on the lens unit, as via a wafer or wafers, may be employed in such determination, and/or modification.

These and other objects and advantages of the invention, as well as the details of an illustrative embodiment, will be more fully understood from the following specification and drawings, in which:

DRAWING DESCRIPTION

FIG. 2 is a plan view of an artificial lens incorporating the features of FIG. 1.

FIG. 3 is a plan view of a modified artificial lens.

FIG. 4 is a plan view of a further modified artificial lens having an external master control.

DETAILED DESCRIPTION

Figure 1:
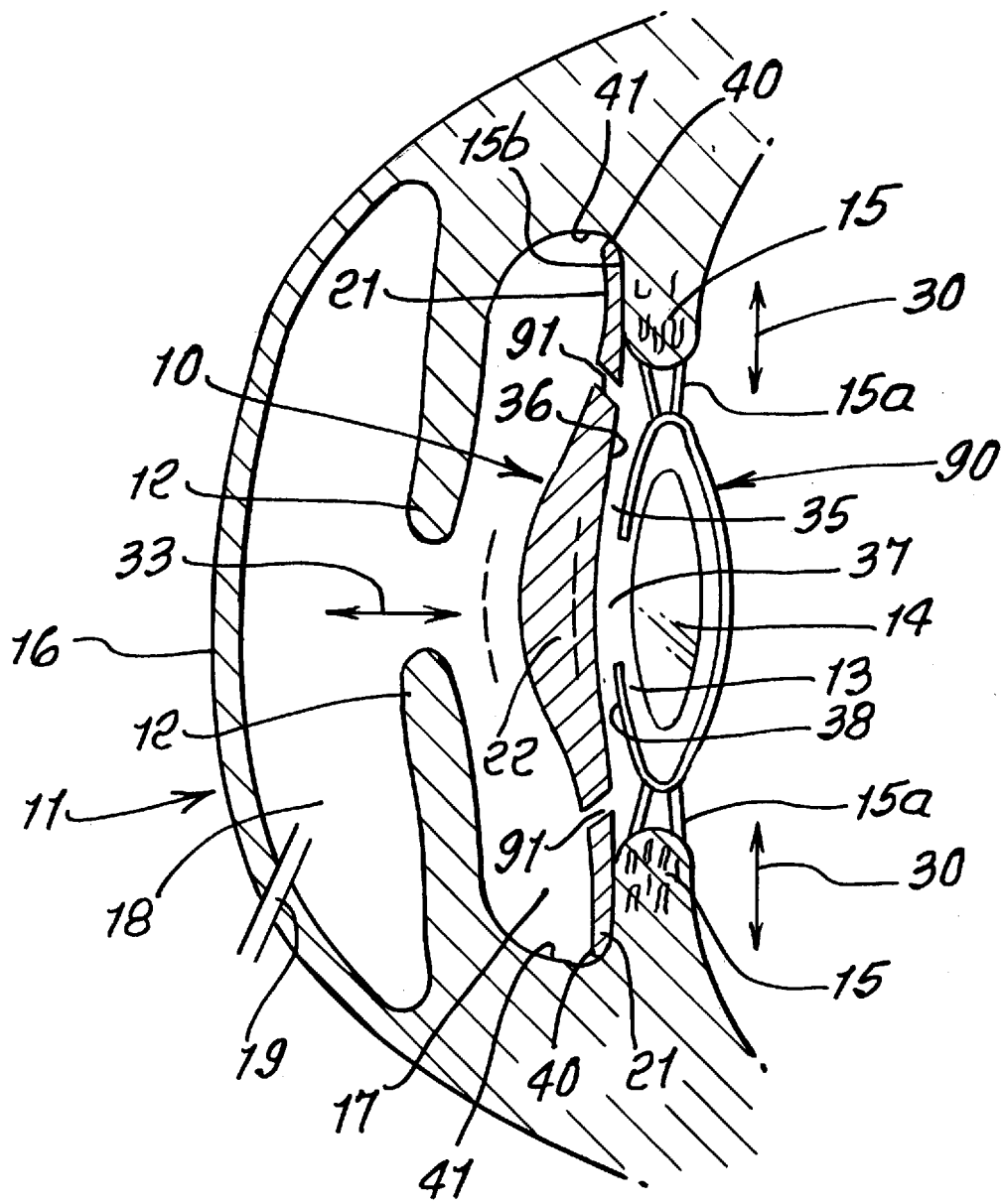
FIG. 1 is a cross section through the eye showing lens unit implantation.

In FIG. 1, the artificial lens unit 10 has been implanted into the eye 11 between the iris 12 and the natural lens zone 13. That zone is shown as including a capsule 90 from which the natural lens has been removed, and a pseudophakic (initially inserted) artificial lens 14 inserted in the capsule. The purpose for inserting lens unit 10 is to improve vision, as by correcting for vision defect associated with artificial lens 14 alone. Eye ciliary muscles are indicated at 15; and they surround the capsule to which they are peripherally attached, as at 15a. The pupil appears at 16. Posterior and anterior eye zones appear at 17 and 18.

A wound 19 in the pupil affords entry of the folded artificial lens unit 10 into the zone 18, from which it is maneuvered into zone 17, to the position shown. Haptics 21 do not engage the iris.

Lens unit 10, which may consist of silicone or equivalent material, has haptics 21, which extend oppositely away from the bead-like lens 22 in front of lens 14. See FIG. 1, for example. The haptics are or become attached or adhered to the forward-facing sides of the ciliary muscles, as at 15b, which provide a platform for haptic attachment. In this regard, the tabular haptics may have roughened surface extents, to face and engage the ciliary muscles, promoting adherence, as via eye tissue growth. One preferred example of such roughened surface extent is the mesh indicated at 25 in FIG. 2.

The haptics have sufficient stiffness to move laterally (see arrows 30) with the ciliary muscles, whose movement controls lateral contraction of the capsule, such lateral movement of the haptics being transmitted to the bulging lens bead 22, to effect its axial longitudinal deflection in the direction of arrows 33. Such deflection is sufficient to cause the lens 22 to refract light rays from an observed object to again focus at a point near the wearer's retina. Also, such lens deflection to obtain proper focusing is made possible by the initial angularity of the haptics, by the stiffness along their lateral extents, and by haptics effective hinging connection to the lens 22, along the bendable, lateral extents of the haptics, between 22 and 21. See FIG. 2.

Note the slight gap 35 between the rear surface 36 of the lens unit 10 and the front window 37 in the capsule, or the capsule surface 38 about the window. The gap contains eye fluid to wet the lenses; and a port or ports 91 may be provided in the haptics to allow eye fluid flow in and out of the gap 35, as before, during, or after lens 22 bodily movement, as described. The haptics may have yieldably flexible outer tips 40 to engage the inner wall 41 of zone 17, to aid in centering the lens unit 10, relative to the lens 14, and to aid in stably positioning the haptic roughened surface portions 25 adjacent the ciliary muscles, during adherence as by tissue growth. The haptics are allowed to adhere to the ciliary muscles so as to maintain the gap 35 between a medial portion of the artificial lens and the natural lens, or its zone; also the artificial lens and haptics are maintained out of contact with the iris, as shown in FIG. 1.

FIG. 3 shows an elongated lens unit 50 having an elongated, asymmetric, light-transmitting, medial lens portion 51, haptics 52 with roughened or mesh-like regions 53, for adherence to ciliary muscles, and eye fluid passing through ports 54. Haptics positioning tips appear at 56, and may be used, as ae tips 40.

Figure 5:
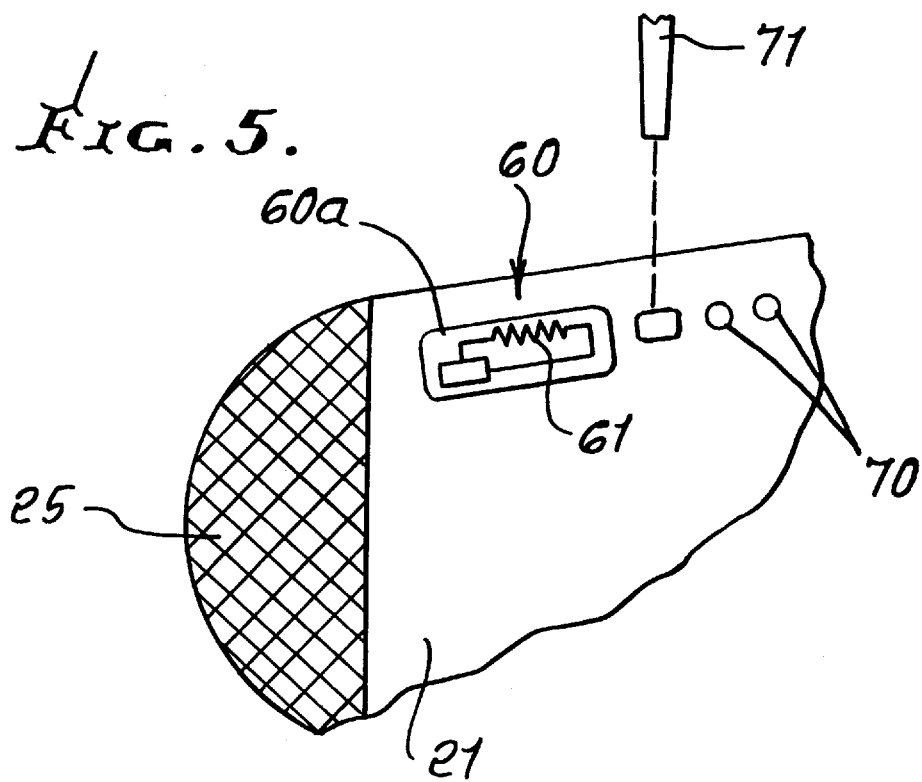
FIG. 5 is an enlarged fragmentary view of a lens unit haptic with electronic circuitry thereon.
Figure 6:
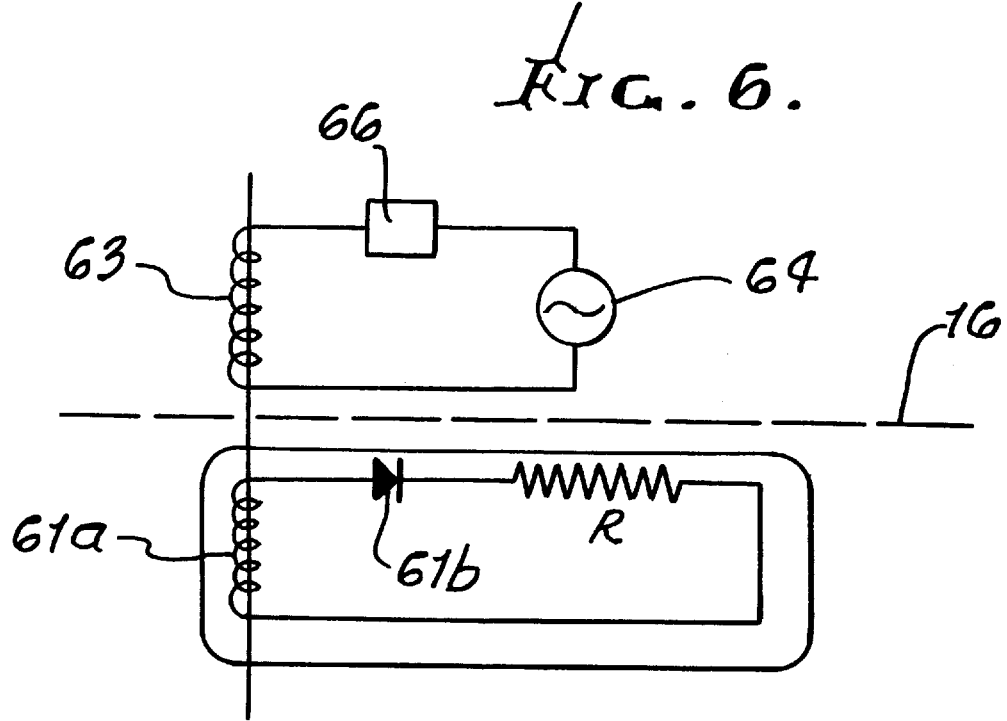
FIG. 6 is a schematic circuit diagram.

FIGS. 4–6 show a unique means to operatively associate electronic or electrical circuitry with the implantable lens unit. In FIG. 4, the lens unit may have a configuration the same as in FIG. 2, for example. See the same identifying numerals applied. Also provided is electrical circuitry, indicated generally at 60, as in or on a wafer 60a attached as by bonding to the lens unit, as at haptics 21. Note the local and symmetrical locations of four such wafers 60a.

An external, master control unit 62 may have electrical or magnetic communication with the circuitry on the four wafers. See four paths or connectors 62a. Microelectronic circuitry may be provided on the wafers to process data or signals. FIG. 5 shows a circuit element 61, such as a resistor. FIG. 6 shows a current source in series with the element 61, the source for example including a coil 61a and a diode 61b. A magnetic field passing through the coil generate current, rectified at 61b and passing through the resistor. An external coil 63 and AC generator 64 generates the magnetic field. See also circuitry 66. The circuitry can be embedded in the wafer and located in or on the haptic.

One example of use is to detect strain, due to deflection in the haptic. The resistor 61 effectively bonded to the haptic, as via the wafer, is stretched as the haptic deflects, changing its resistance. This changes the response to the circuitry, reflected back through coils 61a and 63 and detected at 66, whereby the amount of deflection of the haptic can be determined externally. The use of four such detectors, as at 60a in FIG. 4, and on both haptics, enables accurate determination of inserted lens responsive movement, as the eye ciliary muscles expand and contract.

Such lens movement can then be modified, i.e., "tuned" to conform to a predetermined standard, externally. See for example the lens haptic zones 70 near each wafer, and which can be deformed as by a laser beam 71, to modify local thickness or shape of the haptic, thereby slightly changing its characteristic movement. Zones 70 may, for example, consist of thermo-plastic material, subject to shape change, with temperature increase above a temperature threshold. In this way, accuracy of vision, provided by the lens insert, can be optimized. Other types of circuits 60, and uses thereof, are of course possible and are within the scope of this invention, directed to provision of microcircuitry on an implanted lens unit.

The invention enables testing for the optimum lens insert, as for example by the steps:

a) inserting a first artificial lens into the posterior zone of the eye and temporarily positioned for eye vision correction use, in conjunction with an existing lens at the eye capsule zone, b) thereafter removing the first artificial lens from the eye, and c) inserting a second and different artificial lens into the posterior zone of the eye, and positioned for temporary eye vision corrective use, in conjunction with the existing lens, d) determining that the inserted second lens is more corrective of vision than the first lens, e) and effecting attachment of the second lens to eye structure to maintain the second lens in permanent position for use.

Other existing lens can be a pseudophakic lens, or a lens, such as a natural lens of the eye.

Light-blocking darkened or qpaque zones may be provided on or at or proximate the lens periphery, as for example are indicated at 80 in FIG. 2.

Sensors embedded in the elastomide (synthetic resin) of the lens unit, as for example in haptic structure, will detect activity, such as movement of the ciliary muscle, to which the haptic becomes attached, as described. For example, ciliary muscle contraction, as detected at the multiple points (four as described) of circuit sensor location, is detected, as the lens optic is advanced forwardly, by accommodation, and the reverse occurs when the optic retracts as the ciliary muscle relaxes.

Such sensors can be used to detect rotation of the toric lens. Also, maintenance of immobility of the lens unit and ciliary muscle, as desired during healing, i.e., adhesion attachment of the haptics to the ciliary muscle, can be monitored using such sensors. Local control of lens darkening, using such circuitry with circuit flow between selected points on the lens unit to effect such selected zone darkening is also contemplated.

I claim:

1. The method of providing an artificial lens inserted into the eye between the iris and the natural lens zone, having existing lens there being eye ciliary muscles located peripherally of said zone, that includes
   a) providing said artificial lens to be compliant and to have anterior and posterior surfaces, and haptics extending away from the periphery of the artificial lens,
   b) and inserting said artificial lens to extend into position between the iris and said zone, and to cause said haptics to extend into adjacency to said ciliary muscles, and
   c) allowing said haptics to adhere to said ciliary muscles, so as to maintain a fluid gap between a medial portion of said artificial lens and said natural lens zone, and so as to maintain the artificial lens and haptics spaced from the iris,
   d) whereby subsequent movement of said ciliary muscles causes movement of said haptics transmitted to effect bodily movement of said artificial lens in posterior and anterior directions to change the angularity of refraction of light passing through said artificial lens toward the eye retina.

2. The method of claim 1 wherein the remainder of said artificial lens is maintained free of attachment to said zone.

3. The method of claim 1 wherein said existing lens is a natural lens and, the anterior surface of said artificial lens is maintained free of attachment to said natural lens.

4. The method of claim 1 wherein said existing lens is a second artificial lens and, the anterior surface of said artificial lens having said haptics being maintained free of attachment to said second artificial lens.

5. The method of claim 2 wherein a gap is maintained between a medial portion of said artificial lens and said zone.

6. The method of claim 5 including allowing eye fluid to fill said gap.

7. The method of claim 5 wherein said gap is maintained as said lens is moved in said posterior direction.

8. The method of claim 1 including providing said lens to have a medial, transparent, light-passing zone, and at least one light-blocking zone.

9. The method of claim 1 including maintaining said haptics out of contact with the iris.

10. The method of claim 1 which includes providing said lens surfaces to have one of the following:
    i) both surfaces convex
    ii) both surfaces concave
    iii) one surface convex and the other concave.

11. The method of claim 10 which includes providing said lens to have a medial, transparent zone, which is elongated, and darkened border zones adjacent opposite edges of said medial zone.

12. The method of claim 11 wherein the haptics are provided to be characterized by one of the following:
    i) the haptics project substantially parallel to said medial transparent zone
    ii) the haptics have root ends projecting from edges of said medial transparent zone
    iii) the haptics have root ends substantially tangent to opposite ends of said medial transparent zone
    iv) the haptics project substantially parallel to opposite ends of said medial transparent zone, which is surrounded by said, darkened border zones.

13. The method of claim 5 wherein the artificial lens has a central main portion, including providing porting through said artificial lens to communicate with said gap, for allowing access of eye fluid to said gap, said porting located in sidewardly offset relation to said central main portion.

14. The method of claim 1 wherein said step of allowing the haptics to attach to the ciliary muscles includes allowing outer portions of the haptics to bond to said ciliary muscles.

15. The method of claim 14 including providing said outer portions of the haptics to have mesh configuration.

16. The method of claim 1 including providing said artificial lens to have asymmetric configuration.

17. The method of claim 16 including providing said asymmetric artificial lens to have a light-blocking zone or zones.

18. The method of claim 1 including removing said artificial lens prior to step c) and inserting a different artificial lens characterized as providing better vision, and then allowing said step c) to proceed.

19. The method of claim 1 wherein said attachment is effected by providing roughened surface structure on lens haptic means, and causing said roughened surface structure to attach to eye structure laterally of said pseudophakic lens.

20. The method of claim 1 wherein said artificial lens is provided in the form of an asymmetric lens.

21. The method of claim 1 wherein said artificial lens is provided to have one or more opaque zones to block light transmission.

22. The method of claim 1 including providing miniature electronic circuitry carried by said artificial lens.

23. The method of claim 1 including providing the haptics with yieldably flexible outer tips to aid in stably positioning the lens haptics adjacent the ciliary muscles.

24. The method of claim 1 including providing said lens with at least one light-blocking zone.

25. The method of claim 1 including detecting and modifying a physical characteristic of the artificial lens inserted into the eye.

26. The method of improving eye vision, that includes:
    a) inserting a first artificial lens into the posterior zone of the eye having an existing lens and temporarily positioned for eye vision correction use, in conjunction with an existing lens at the eye capsule zone, b) thereafter removing said first artificial lens from the eye, and c) inserting a second and different artificial lens into the posterior zone of the eye, and positioned for temporary eye vision corrective use, in conjunction with said existing lens, d) determining that said inserted second lens is more corrective of vision than said first lens, e) and effecting attachment of the second lens to eye structure to maintain the second lens in permanent position for use and in spaced relation to said existing lens and to the iris of the eye.

27. The method of claim 26 wherein said attachment is to eye ciliary muscle structure.

28. The method of claim 26 wherein said attachment is effected by providing roughened surface structure on lens haptic means, and causing said roughened surface structure to attach to eye structure laterally of said existing lens.

29. The method of claim 26 wherein at least one of said first and second lenses is provided in the form of an asymmetric lens.

30. The method of claim 26 wherein at least one of said lenses is provided to have one or more opaque zones to block light transmission.

31. The method of claim 26 including providing miniature electronic circuitry carried by at least one of said lenses.

* * * * *